United States Patent
Donaldson

(10) Patent No.: US 10,182,715 B2
(45) Date of Patent: Jan. 22, 2019

(54) APPARATUS AND METHOD FOR ASSESSING AND IMPROVING THE RELIABILITY OF A VISUAL FIELD TEST

(71) Applicant: Ibisvision Limited, Aberdeen (GB)

(72) Inventor: Blair Donaldson, Aberdeen (GB)

(73) Assignee: IBISVISION LIMITED (GB)

( * ) Notice: Subject to any disclaimer, the term of this patent is extended or adjusted under 35 U.S.C. 154(b) by 0 days.

(21) Appl. No.: 14/911,134

(22) PCT Filed: Aug. 1, 2014

(86) PCT No.: PCT/GB2014/052369
§ 371 (c)(1),
(2) Date: Feb. 9, 2016

(87) PCT Pub. No.: WO2015/019065
PCT Pub. Date: Feb. 12, 2015

(65) Prior Publication Data
US 2016/0183781 A1   Jun. 30, 2016

(30) Foreign Application Priority Data
Aug. 9, 2013   (GB) .................................. 1314308.6

(51) Int. Cl.
*A61B 3/02* (2006.01)
*A61B 3/00* (2006.01)
*A61B 3/10* (2006.01)
*A61B 3/024* (2006.01)

(52) U.S. Cl.
CPC ............ *A61B 3/024* (2013.01); *A61B 3/0025* (2013.01); *A61B 3/0041* (2013.01); *A61B 3/0091* (2013.01)

(58) Field of Classification Search
CPC ....... A61B 3/024; A61B 3/1225; A61B 3/032; A61B 3/103; A61B 3/14; A61B 3/113; A61B 3/02; A61B 3/18; A61B 3/1015; A61H 5/00
USPC ....... 351/224, 223, 221, 222, 200, 203, 205, 351/206, 209–211, 239, 243–246
See application file for complete search history.

(56) References Cited

U.S. PATENT DOCUMENTS

| | | | |
|---|---|---|---|
| 3,984,156 A | 10/1976 | Jernigan | |
| 4,260,227 A | 4/1981 | Munnerlyn et al. | |
| 4,854,694 A | 8/1989 | Hirano et al. | |
| 5,220,361 A * | 6/1993 | Lehmer | A61B 3/113 351/210 |
| 2004/0057013 A1 * | 3/2004 | Cappo | A61B 3/024 351/224 |
| 2010/0002192 A1 * | 1/2010 | Hara | A61B 3/0091 351/224 |

* cited by examiner

*Primary Examiner* — Dawayne A Pinkney
(74) *Attorney, Agent, or Firm* — Laubscher & Laubscher, P.C.

(57) ABSTRACT

Apparatus for testing a patient's visual field, the apparatus comprising: means for recording the results of the patient's responses to one or more visual field targets (5) presented during a visual field test; and a fixation loss switch activatable by an observer observing the patient during the visual field test for identifying periods of fixation loss by the patient. The results recorded during periods of fixation loss are identified as being unreliable. Also disclosed is a method of testing a patient's visual field.

16 Claims, 2 Drawing Sheets

APPARATUS AND METHOD FOR ASSESSING AND IMPROVING THE RELIABILITY OF A VISUAL FIELD TEST

This application is a § 371 national phase of PCT International Application No. PCT/GB2014/052369 filed Aug. 1, 2014. PCT/GB2014/052369 claims priority to GB Application No. 1314308.6 filed Aug. 9, 2013. The entire contents of these applications are incorporated herein by reference.

The present invention relates to a visual field testing apparatus and method and, in particular, a visual field testing apparatus and method which improves the reliability of the results of the visual field test.

With conventional apparatus, during testing of a patient's visual field they are asked to direct their gaze towards a fixation target. A visual field target is then presented at another location in what would be within a normal visual field. The patient is instructed to give a response such as pressing a switch or, with a field test using a LCD screen, moving a cursor over the new visual field target if they see the newly presented visual field target. However, when the patient suffers a loss of fixation, such as when their direction of gaze moves away from the requested direction or when the patient has reduced concentration, the test result at that visual field target position may be invalid.

In this respect, if the patient's direction of gaze moves away from their fixation target and closer to a visual field target, the patient may become aware of visual field targets that they would not otherwise be aware of if they had still been looking at the requested fixation target. The patient would therefore give a positive response, which would be a false positive result.

Furthermore, if the patient loses concentration, they may not respond to the presentation of a visual field target that they would have otherwise registered as seen had they been concentrating fully on the test. This response would be a false negative.

Accordingly, due to the presence of such false positive and false negative results, it can be difficult for a practitioner to accurately analyse the results of a visual field test since they are unable to assess how reliable the results are.

There have therefore been several methods which aim to assess the reliability of visual field test results.

For example, in one method, a visual field target can be presented in an area which is known to be a blind spot to a normal person. If the patient sees the target in the blind spot area, it is therefore determined that they must not be looking directly at the requested fixation target. The blind spot target is then presented several times during a test to provide a general indication of the reliability of the test. However, this method cannot indicate the reliability of each individual field test target result. Furthermore, the position of the blind spot in a patient can vary from person to person and so the results of this method can sometimes be inaccurate.

WO 2012/146710 describes another method in which a video recording of the patient's eye being tested is taken during a visual field test. When the practitioner identifies positive visual field test results which are unexpected, and they therefore suspect may be inaccurate, they can then examine the video recording by reviewing footage coinciding with the display of that visual field target to determine if the patient's fixation was satisfactory. This method, however, has a number of limitations. Firstly, it does not help the practitioner to identify false negative results that may occur, for example, due to a loss of concentration. This is because the visual field target will merely be recorded as not seen by the patient and hence would not be suspicious to the practitioner. The practitioner would therefore not be prompted to review the video recording to determine if fixation for that target was satisfactory. Secondly, this method significantly increases the time taken by a practitioner to examine the visual field results since they may need to check the validity of multiple test target results. Thirdly, the recording of video images of the patient's eye together with the actual test results will lead to much larger file sizes and an increased data processing burden. This results in greater overheads for visual field testing facilities.

The present invention therefore seeks to overcome the above limitations and provide a method and apparatus which improves the reliability of visual field test results.

According to a first aspect of the present invention, there is provided visual field testing apparatus for testing a patient's visual field, the apparatus comprising:

recording means for recording the results of the patient's responses to one or more visual field targets presented during a visual field test; and a fixation loss switch activatable by an observer observing the patient during the visual field test for identifying periods of fixation loss by the patient;

wherein results recorded during periods of fixation loss are identified as being unreliable.

In this way, the reliability of visual field test results is determined in real-time during the test. That is, results of a patient seeing or not seeing targets during periods of fixation loss can be identified by measurements taken during the test itself. This is then used to identify inaccuracies caused by fixation loss where the patient has, for example, blinked, moved out of the correct position, or lost concentration. The above provides a number of advantages.

Firstly, the present invention avoids the need for extensive post test analysis by a practitioner. Unreliable results are automatically identified, thereby allowing a practitioner to immediately assess the result of a patient's visual field test with a high level of confidence.

Secondly, the present invention also allows for both false positive and false negative results to be detected. This is because the activation of the fixation loss switch by the observer identifies all periods of fixation loss, regardless of whether those periods coincide with a patient seeing or not seeing a particular visual field target. As such, the present invention does not rely on a practitioner guessing if the patient lost fixation during the display of a particular target.

Thirdly, with the present invention, the observer is also only required to observe the patient's fixation during the visual field test and identify periods of fixation loss independent of the progress of the test. As such, the observer does not need to be aware of when targets are being displayed during the visual field test itself. There is therefore a low burden on the observer, allowing for a high level of accuracy to be achieved.

Fourthly, with the present invention, only a small amount of data needs to be recorded in addition to the visual field test results since only periods of observed fixation loss are recorded. This contrasts with prior systems which rely upon storing a video record of the test for review.

Finally, the presence of the observer also does not incur any additional burden since they are typically required to be present anyway. That is, the observer is required to ensure that the patient is in the correct position with relation to the visual testing apparatus and to explain the visual test itself. As the visual field test lasts only a few minutes, the observer usually does not have time to leave the patient. Consequently, the present invention makes use of a previously unused resource.

Preferably, the apparatus further comprises a correlator for correlating periods of fixation loss with a time line representing the presentation of visual field targets during a visual field test and marking results during those periods of fixation loss to identify them as unreliable. In this way, the practitioner can review how fixation accuracy varies throughout the test and see how this influences the overall test results. The marked results may, for example, then be highlighted or recorded in a different colour to reliable results.

Preferably, the observer's reaction time in activating the fixation loss switch is compensated for when identifying periods of fixation loss. In this way, observer delay is accounted for so that results for targets displayed adjacent to periods of activation of the fixation loss switch are accurately processed.

Preferably, the apparatus further comprises an output for outputting the visual field test results.

Conveniently, the output may output the visual field test results in the form of a visual field map, with unreliable results being distinguished from reliable results in the visual field map. In this way, a practitioner analysing the results of the patient's responses to the visual field test is easily able determine the reliability of the results in different areas of the visual field map.

Conveniently, the output may output the visual field test results in a time line correlated against a time line mapping periods of fixation loss. In this way, the results of the patient's responses to the visual field test are presented for analysis by the practitioner such that the practitioner can quickly and easily determine the periods of the test where the patient has lost fixation. Furthermore, the time line allows the practitioner to determine whether a re-test is necessary, for example, if the patient had lost fixation for a significant length of time during the test. This may, for example, be used to alter the parameters of subsequent tests, such as test length or to focus a subsequent test on a specific visual field region.

Conveniently, the output may output the results from more than one visual field test in the form of an optimised visual field map. In this way, the results of the patient's responses from more than one visual field test can be combined in the form of a composite visual field map. This would allow, for example, results from one test target identified by the observer as unreliable to be eliminated or replaced with reliable results from another test. Consequently, an optimised visual field map can be produced for analysis by a practitioner, allowing the practitioner greater confidence in the reliability of the patient's responses.

Preferably, the output outputs the optimised visual field map by automatically selecting the most reliable visual field test result for each visual field test target position. In this way, if a visual field test is performed more than one time on a patient, the output analyses the plurality of visual field test results in each position across the tests and automatically selects the most reliable result for output in the optimised visual field map. As such, any unreliable results can be automatically eliminated and replaced with reliable results from other tests. Furthermore, if there are a number of a reliable results for a visual field target, the output selects and outputs the result closest to the normative value for that target. The output may be part of a processing system.

Preferably, the apparatus further comprises a monitoring arrangement for facilitating the observer to monitor the patient's fixation during the visual field test. In this way, the observer may observe the patient in a way that minimises or avoids any adverse influence on the results of the visual field test.

Preferably, the monitoring arrangement comprises a display for displaying to the observer a real time image of the patient's eye during the test. In this way, the observer can easily focus on observing the patient's eye to identify a loss of fixation.

Preferably, the display of a visual field target during the visual field test is repeated if the result of the patient's response is identified as unreliable. In this way, since it can be determined in real-time if the result of a patient's response to a visual field target is unreliable, the visual field test can be automatically modified on the fly to re-test targets with unreliable results.

Furthermore, if the results from a particular visual field target position are inconsistent across a number of tests, the visual field test may be repeated multiple times, scrutinising that target position by repeating the display of targets in that locality until a sufficient level of confidence has been achieved.

According to a second aspect of the present invention, there is provided a method of testing a patient's visual field, the method comprising:

recording the results of patient responses to one or more visual field targets presented during the visual field test;

providing a fixation loss switch activatable by an observer observing the patient during the visual field test where activation of the switch identifies a period of fixation loss by the patient; and identifying results recorded during periods of fixation loss as being unreliable.

Preferably, the method further comprises the step of correlating periods of fixation loss with a time line representing the presentation of visual field targets during a visual field test and marking results during those periods of fixation loss to identify them as unreliable.

Preferably, the observer's reaction time in activating the fixation loss switch is compensated for when identifying periods of fixation loss.

Preferably, the method further comprises the step of outputting the visual field test results.

Conveniently, the output may output the visual field test results in the form of a visual field map, with unreliable results being distinguished from reliable results in the visual field map.

Conveniently, the output may output the visual field test results in a time line correlated against a time line mapping periods of fixation loss.

Conveniently, the output may output the results from more than one visual field test in the form of composite visual field map.

Preferably, the output outputs the optimised visual field map by automatically selecting the most reliable visual field test result for each visual field test target position.

Preferably, the method further comprises the step of providing a monitoring arrangement for facilitating the observer to monitor the patient's fixation during the visual field test.

Preferably, the monitoring arrangement comprises a display for displaying to the observer a real time image of the patient's eye during the test.

Preferably, the method further comprises the step of repeating the display of a visual field target during the visual field test if the result of the patient's response is identified as unreliable.

Illustrative embodiments of the present invention will now be described with reference to the accompanying drawings in which.

Figure 1:
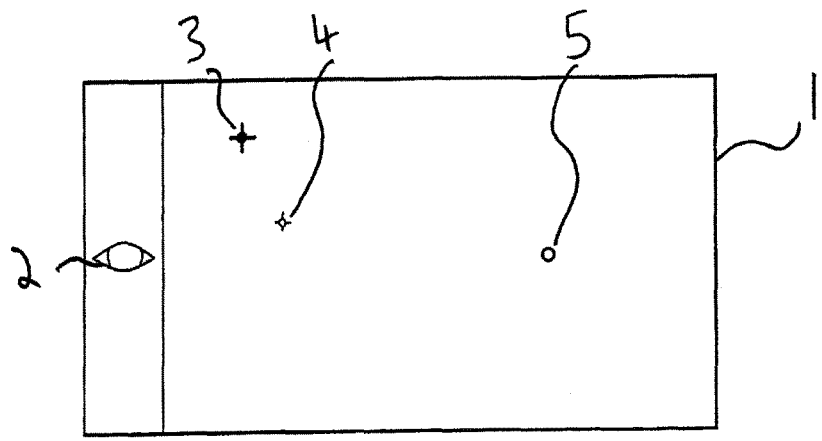
FIG. 1 shows a schematic representation of a visual field test display screen during a visual field test.

FIG. 1 shows a schematic representation of a visual field test display screen 1 as seen by a patient during a visual field test. In this embodiment, a real-time video image of the patient's eye being tested 2 is displayed on the display screen 1 for viewing by an observer. In this case, the video image 2 is on the left side of the display screen 1, although it could be displayed anywhere on the display screen 1 where it doesn't interfere with the patient's part of the visual field test.

Figure 3:
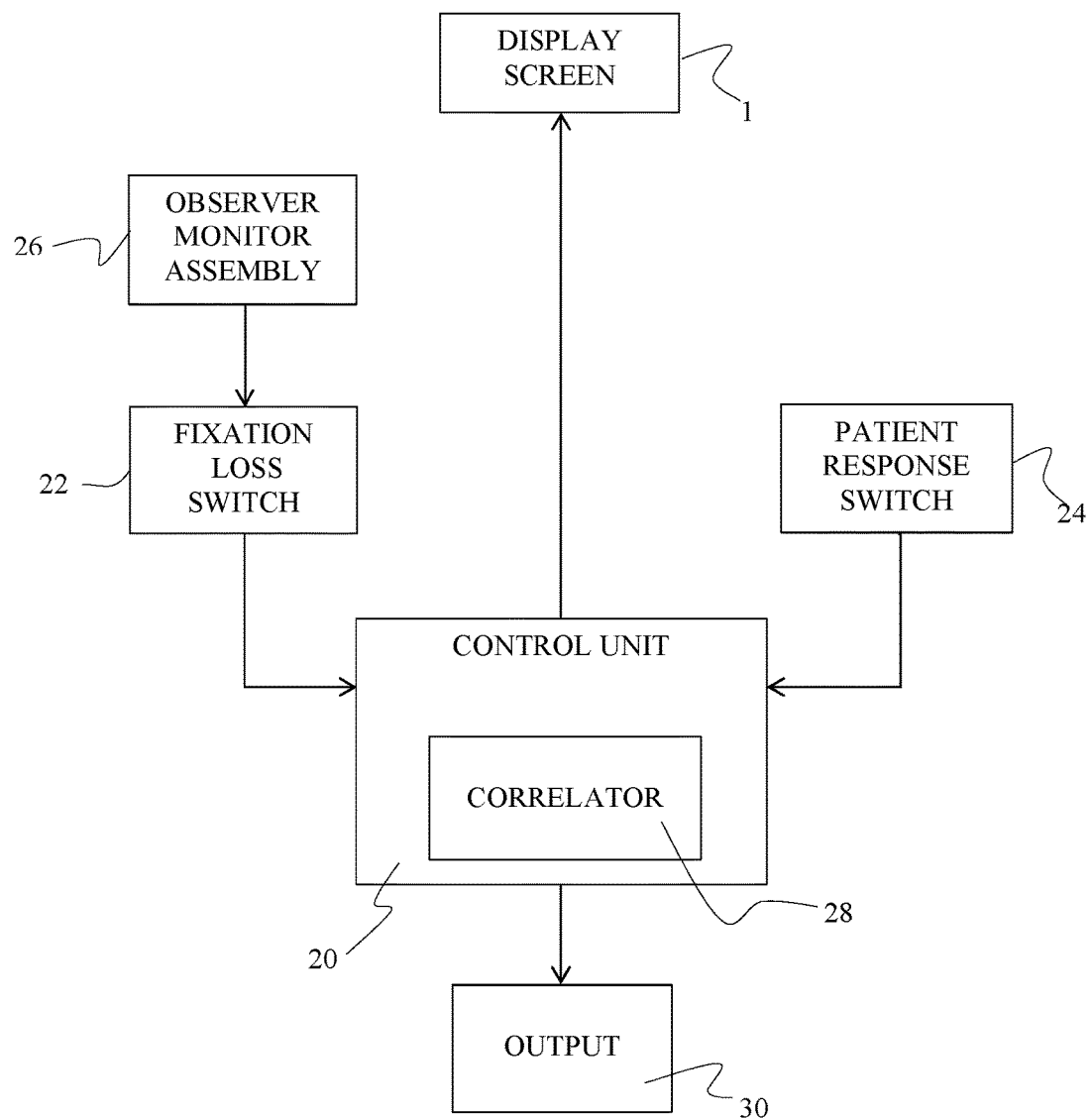
FIG. 3 is a block diagram of the apparatus for testing a patent's visual field.

As well as the display 1, the apparatus also comprises a control unit 20, a fixation loss switch 22 and a patient response means as shown in FIG. 3. In this embodiment, the patient response means is provided as a patient response switch 24, however in other embodiments it may be provided as, for example, an input device such as a mouse or touch screen, which may be used to move a cursor over a field target shown on the display for example. The control unit controls the presentation of targets on the display, and processes inputs received from the patient using the patient response switch and from an observer using the fixation loss switch.

During the visual field test, the patient is asked to fixate on a fixation target 3 whilst a series of visual field targets 5 are displayed on the display screen 1. The patent then registers when they see visual field targets 5 within their field of vision using the patient response switch.

At the same time as the visual field test is running, an observer, such as a human or an electronic or automated device, is asked to observe the patient's eye via an observer monitor 26. If the observer detects fixation loss by the patient, the observer activates the fixation loss switch 22 by depressing it. When fixation returns, the observer releases the switch. The period of time in which the switch is activated is identified as a period of fixation loss by the control unit. As discussed below, these periods of fixation loss are then correlated or mapped against the results of whether the patent has seen or not seen individual visual field targets during the test to assess their reliability.

A correlator 28 within the processing unit correlates the periods of fixation loss with a time line of the visual field test so that results for targets presented during the test are automatically identified and recorded as unreliable.

As an example, in use, the display screen 1 in FIG. 1 shows a presented visual field target 5 that would be located such that if the patient is looking at the fixation target 3, the visual field target 5 would be in the patient's blind spot. Accordingly, there should be no response from the patient, and the result should be that the target will register as not seen in the visual field test.

However, if the patient has lost fixation and their actual direction of gaze is represented by point 4, the patient would see the visual field target 5 and respond positively. This would be a false positive result. However, with the present invention, since the patient will have lost fixation on the fixation target 3, the observer will have activated the fixation loss switch to identify a loss of fixation. Consequently, the above false positive result will be recorded as unreliable. As such, this result may be discounted from the visual field map output.

Figure 2:
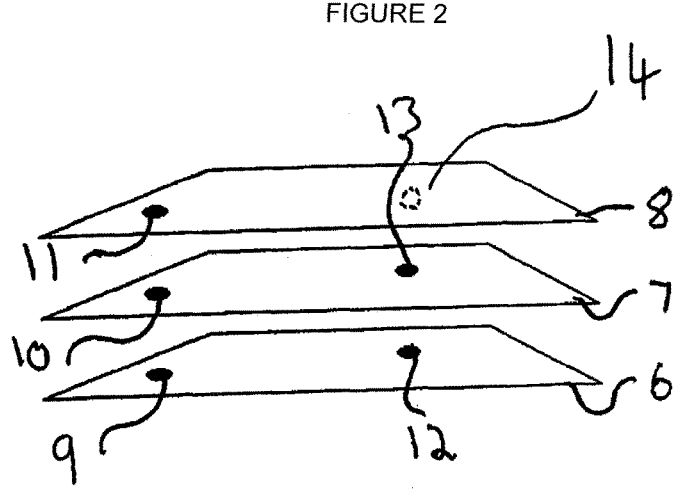
FIG. 2 shows a schematic representation of three visual field maps of the results of three visual field tests on the same patient.

FIG. 2 shows a schematic representation of three visual field maps 6, 7, 8 compiled from three sets of results from three visual field tests on the same patient. The first 6, second 7 and third 8 visual field maps overlay each other such that the visual field maps 6, 7, 8 can be assessed simultaneously in a composite visual field map. This allows an optimised visual field map to be formed and displayed on an output 30 whereby, for example, unreliable results from one test can be eliminated and replaced with reliable results from other tests, In this example, the left test results 9, 10, 11 all represent the patient's response to the same left visual field target. The black circles indicate that the left target was unseen by the patient in all three visual field tests, while the observer has not identified any periods of fixation loss. As such, the left side results can be registered as unseen, identifying to a high degree of accuracy that there is a lack of visual field in this region.

The right visual field results 12, 13 both represent the patient's responses to the same right visual field target. The results in the first 6 and second 7 visual field maps indicate that the right target was unseen by the patient in the first and second tests. However, the third visual field map 8 indicates that the right target was seen by the patient in the third test. However, this result 14 is marked as being during a period of fixation loss. Consequently, the positive result in this test can be discarded.

However, in an alternative case, if the observer has instead identified that the patient lost fixation during the period that the right target was presented in the first and second visual field tests, results 12 and 13, these results would have been recorded as unreliable and the patient's positive response 14 to the third field test could be taken as the accurate response.

In this way, an optimised visual field map can be produced automatically by the system software by using the results of more than one visual field test to display the most reliable result for each test target position on the output.

It will be understood that the embodiment illustrated above shows applications of the invention only for the purposes of illustration. In practice the invention may be applied to many different configurations, the detailed embodiments being straightforward for those skilled in the art to implement.

For example, the video image of the patient being observed by the observer could be displayed on a separate display to the visual field test to ensure that the patient is not disturbed by the observer and so the visual field test results are not affected.

In addition, although in the above example only one eye has been observed, in other embodiments both of the patient's eyes could be observed simultaneously.

Furthermore, the process of generating the optimised visual field map may be used to automatically control subsequent visual field testing procedures on the patient. For example, if the results from a particular visual field target position are inconsistent across a number of tests, the system may automatically modify subsequent tests to further scrutinise that target position by repeating the display of targets in that locality until a sufficient level of confidence has been achieved.

The invention claimed is:

1. Visual field testing apparatus for testing a patient's visual field, comprising a patient response switch for recording the results of the patient's responses to at least one visual field target presented to the patient during a visual field test;

an observer monitor for displaying to a human observer a real time image of the patient's eye during the visual field test;

a fixation loss switch for recording periods of fixation loss during the visual field test, wherein said fixation loss switch is activatable by the observer when the observer identifies periods of fixation loss by observing the real time image of the patient's eye during the visual field test; and a correlator connected with said patient response switch and with said fixation loss switch to correlate periods of fixation loss identified by the observer observing the real time image of the patient's eye during the visual field test with a time line representing the presentation of visual field targets during the visual field test to identify patient results during periods of fixation loss as unreliable.

2. Apparatus according to claim 1, wherein the observer's reaction time in activating the fixation loss switch is compensated for when identifying periods of fixation loss.

3. Apparatus according to claim 1, further comprising an output for outputting the visual field test results.

4. Apparatus according to claim 3, wherein the visual field test results are output in the form of a visual field map, with unreliable results being distinguished from reliable results in the visual field Map.

5. Apparatus according to claim 3, wherein the visual field test results are output in a time line correlated against a time line mapping periods of fixation loss.

6. Apparatus according to claim 3, wherein the results from more than one visual field test are output in the form of an optimised visual field map.

7. Apparatus according to claim 6, wherein the optimised visual field map is output by automatically selecting the most reliable visual field test result for each visual field test target position.

8. Apparatus according to claim 1, wherein the display of a visual field target during the visual field test is repeated if the result of the patient's response is identified as unreliable.

9. A method of testing a patient's visual field, comprising the steps of recording the results of the patient's responses to at least one visual field target presented to the patient during a visual field test;

displaying to a human observer a real time image of the patient's eye during the visual field test;

providing a fixation loss switch for recording periods of fixation loss during the visual field test, wherein the fixation loss switch is activatable by the observer when the observer identifies periods of fixation loss by observing the real time image of the patient's eye during the visual field test;

correlating periods of fixation loss identified by the observer observing the real time image of the patent's eye during the visual field test with a time line representing the presentation of visual field targets during the visual field test; and identifying results recorded during periods of fixation loss as being unreliable.

10. A method according to claim 9, wherein the observer's reaction time in activating the fixation loss switch is compensated for when identifying periods of fixation loss.

11. A method according to claim 9, and further comprising the step of outputting the visual field test results.

12. A method according to claim 11, and further comprising the step of outputting the visual field test results in the form of a visual field map, with unreliable results being distinguished from reliable results in the visual field map.

13. A method according to claim 11, wherein the visual field test results are output in a time line correlated against a time line mapping periods of fixation loss.

14. A method according to claim 11, wherein the results from more than one visual field test are output in the form of an optimised visual field map.

15. A method according to claim 14, wherein the optimised visual field map is output by automatically selecting the most reliable visual field test result for each visual field test target position.

16. A method according to claim 9, and further comprising the step of repeating the display of a visual field target during the visual field test if the result of the patient's response is identified as unreliable.

* * * * *